US009782555B2

(12) United States Patent
Burk et al.

(10) Patent No.: US 9,782,555 B2
(45) Date of Patent: Oct. 10, 2017

(54) EXHALATION SCAVENGING THERAPY MASK

(71) Applicant: TELEFLEX MEDICAL INCORPORATED, Research Triangle Park, NC (US)

(72) Inventors: Marc Alan Burk, Menifee, CA (US); Daniel Patrick Dwyer, Raleigh, NC (US); Gary James Roth, Wake Forest, NC (US); Hyung Joo Lee, Hillsborough, NC (US); John Edward Moenning, Jr., Fishers, IN (US)

(73) Assignee: TELEFLEX MEDICAL INCORPORATED, Research Triangle Park, NC (US)

( * ) Notice: Subject to any disclaimer, the term of this patent is extended or adjusted under 35 U.S.C. 154(b) by 546 days.

(21) Appl. No.: 14/201,533

(22) Filed: Mar. 7, 2014

(65) Prior Publication Data
US 2014/0251333 A1 Sep. 11, 2014

Related U.S. Application Data

(60) Provisional application No. 61/774,665, filed on Mar. 8, 2013.

(51) Int. Cl.
A62B 7/10 (2006.01)
A61M 16/08 (2006.01)
(Continued)

(52) U.S. Cl.
CPC ...... A61M 16/0816 (2013.01); A61M 16/009 (2013.01); A61M 16/06 (2013.01);
(Continued)

(58) Field of Classification Search
CPC .............. A61M 16/0816; A61M 16/06; A61M 16/009; A61M 16/208; A61M 2202/0208;
(Continued)

(56) References Cited

U.S. PATENT DOCUMENTS 1,044,031 A 11/1912 Drager
2,868,198 A 1/1959 Brooke
(Continued)

FOREIGN PATENT DOCUMENTS

EP 1640034 A1 3/2006
WO 2011/078703 A1 6/2011

Primary Examiner — Bradley Philips
Assistant Examiner — Victoria Leszczak
(74) Attorney, Agent, or Firm — Baker & Hostetler LLP

(57) ABSTRACT

A respiratory mask for a medical patient including a shell and a flow coupling is disclosed. The shell includes an upper portion configured to cover a nose of the patient and a lower portion configured to cover a mouth of the patient, where an internal surface of the shell defines an interior volume of the respiratory mask. The flow coupling includes a body, a supply flow passage extending through the flow coupling, a scavenging flow passage extending through the flow coupling, and a septum within the body that separates the supply flow passage from the scavenging flow passage. The supply flow passage and the scavenging flow passage are fluidly coupled to an aperture that extends through the upper portion of the shell, and an aperture extending through the lower portion of the shell, respectively.

20 Claims, 5 Drawing Sheets

(51) Int. Cl.
*A61M 16/00* (2006.01)
*A61M 16/06* (2006.01)
A61M 16/20 (2006.01)
A61M 16/10 (2006.01)

(52) U.S. Cl.
CPC ....... *A61M 16/0672* (2014.02); *A61M 16/085* (2014.02); *A61M 16/1065* (2014.02); *A61M 16/208* (2013.01); *A61M 2202/0208* (2013.01); *A61M 2202/0241* (2013.01); *A61M 2230/432* (2013.01)

(58) Field of Classification Search
CPC ........ A61M 16/0672; A61M 2230/432; A61M 16/1065; A61M 2202/0241; A61M 16/085; A61M 2016/102; A61M 2016/1025; A61M 2016/103; A61M 2016/1035; A61M 16/104; A61M 2039/1072
See application file for complete search history.

(56) References Cited

U.S. PATENT DOCUMENTS

| | | |
|---|---|---|
| 3,747,599 A | 7/1973 | Malmin |
| 4,248,218 A * | 2/1981 | Fischer ............. A61M 16/0666 128/204.18 |
| 4,265,239 A | 5/1981 | Fischer, Jr. et al. |
| 4,770,169 A | 9/1988 | Schmoegner et al. |
| 4,794,921 A | 1/1989 | Lindkvist |
| 4,807,617 A | 2/1989 | Nesti |
| 4,895,172 A | 1/1990 | Lindkvist |
| 4,945,906 A | 8/1990 | Lindkvist |
| 4,949,714 A | 8/1990 | Orr |
| 5,005,571 A | 4/1991 | Dietz |
| 5,265,595 A | 11/1993 | Rudolph |
| 5,311,862 A | 5/1994 | Blasdell et al. |
| 5,322,059 A | 6/1994 | Walther |
| 5,370,110 A | 12/1994 | Corn |
| 5,400,781 A | 3/1995 | Davenport |
| 5,404,873 A | 4/1995 | Leagre et al. |
| 5,419,317 A | 5/1995 | Blasdell et al. |
| 5,474,060 A | 12/1995 | Evans |
| 5,513,632 A | 5/1996 | Nepon et al. |
| 5,560,354 A | 10/1996 | Berthon-Jones et al. |
| 5,676,133 A | 10/1997 | Hickle et al. |
| 5,715,813 A | 2/1998 | Guevrekian |
| 5,823,184 A | 10/1998 | Gross |
| 6,076,524 A | 6/2000 | Corn |
| 6,123,071 A | 9/2000 | Berthon-Jones et al. |
| 6,209,539 B1 | 4/2001 | Loescher et al. |
| 6,237,596 B1 | 5/2001 | Bohmfalk |
| 6,263,874 B1 | 7/2001 | LeDez et al. |
| 6,357,437 B1 | 3/2002 | Jacques |
| 6,398,266 B1 | 6/2002 | Crump |
| 6,439,230 B1 | 8/2002 | Gunaratnam et al. |
| 6,615,830 B1 | 9/2003 | Serowski et al. |
| 6,691,707 B1 | 2/2004 | Gunaratnam et al. |
| 6,698,427 B1 | 3/2004 | Clowers |
| 6,736,140 B1 | 5/2004 | Baczkowski |
| 7,004,163 B2 | 2/2006 | Nashed |
| 7,004,168 B2 | 2/2006 | Mace et al. |
| 7,011,090 B2 | 3/2006 | Drew et al. |
| 7,114,498 B2 | 10/2006 | Nashed |
| 7,178,521 B2 | 2/2007 | Burrow et al. |
| 7,278,423 B2 | 10/2007 | Serowski et al. |
| 7,316,230 B2 | 1/2008 | Drew et al. |
| 7,481,221 B2 | 1/2009 | Kullik et al. |
| 7,513,252 B2 | 4/2009 | Berg |
| 7,559,323 B2 | 7/2009 | Hacke et al. |
| 7,597,100 B2 | 10/2009 | Ging et al. |
| 7,669,599 B2 | 3/2010 | Gunaratnam et al. |
| 7,726,309 B2 | 6/2010 | Ho et al. |
| 7,997,267 B2 | 8/2011 | Ging et al. |
| 8,136,523 B2 | 3/2012 | Rudolph |
| 8,220,458 B2 | 7/2012 | Landis et al. |
| 8,251,058 B2 | 8/2012 | Bird |
| 8,291,905 B2 | 10/2012 | Moenning, Jr. |
| 8,353,293 B1 | 1/2013 | Fuhrman |
| 8,365,734 B1 | 2/2013 | Lehman |
| 2007/0023040 A1 | 2/2007 | Nashed |
| 2007/0125379 A1 | 6/2007 | Pierro et al. |
| 2009/0165799 A1 | 7/2009 | Duquette et al. |
| 2009/0235932 A1 | 9/2009 | Nashed |
| 2009/0266357 A1 | 10/2009 | Varis et al. |
| 2009/0301484 A1 | 12/2009 | Dunlop |
| 2010/0122704 A1* | 5/2010 | Moenning, Jr. ....... A61M 16/06 128/206.24 |
| 2010/0132706 A1 | 6/2010 | Nashed |
| 2010/0147302 A1 | 6/2010 | Selvarajan et al. |
| 2010/0229861 A1 | 9/2010 | Nashed |
| 2011/0155133 A1 | 6/2011 | Barnes et al. |
| 2012/0227736 A1 | 9/2012 | Bowsher |
| 2012/0272954 A1 | 11/2012 | Landis et al. |
| 2012/0285453 A1 | 11/2012 | Bird |
| 2012/0304985 A1 | 12/2012 | Lalonde |
| 2012/0318272 A1 | 12/2012 | Ho et al. |
| 2013/0032153 A1 | 2/2013 | Neely |

* cited by examiner

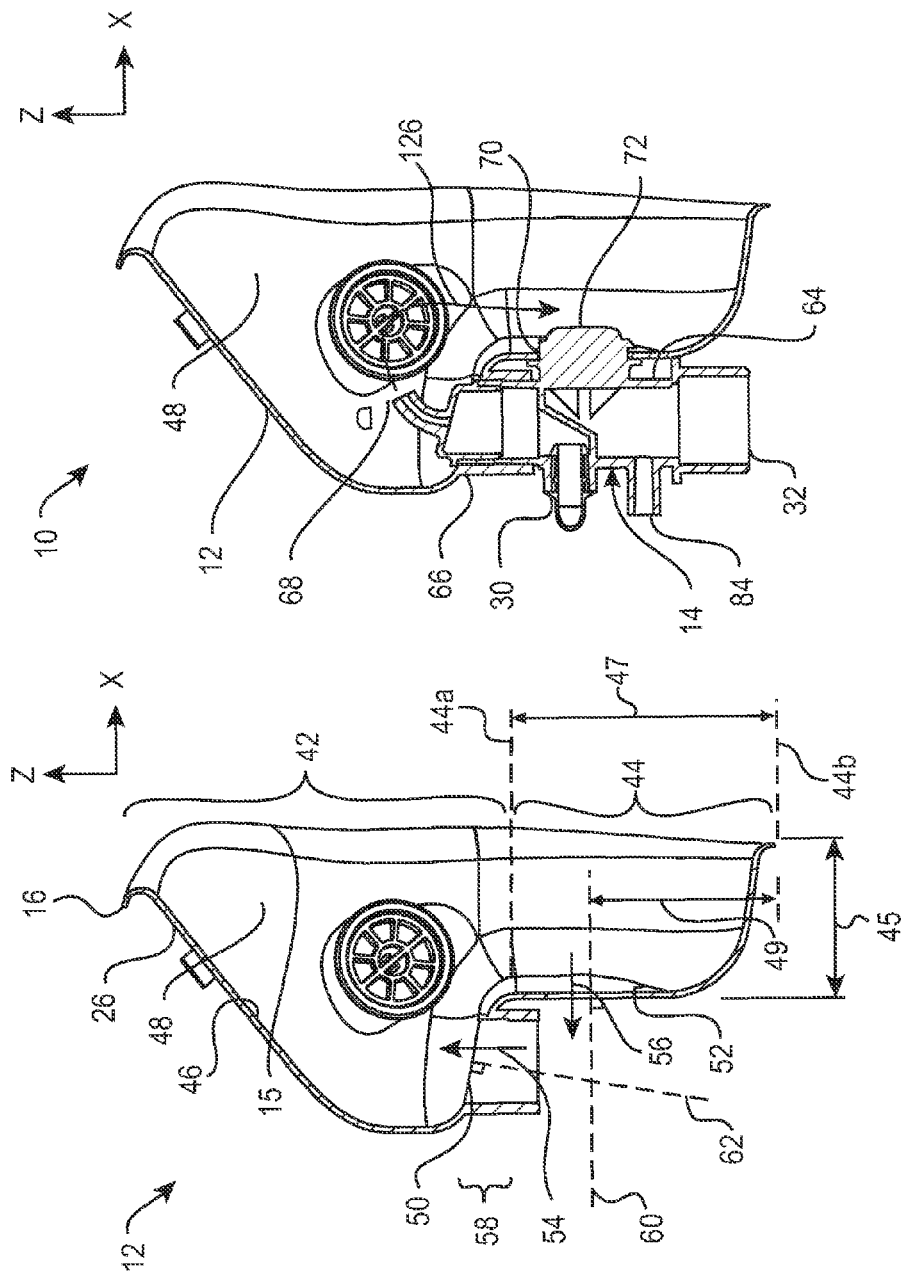

EXHALATION SCAVENGING THERAPY MASK

CROSS-REFERENCE TO RELATED APPLICATIONS

This application claims priority to U.S. Provisional Patent Application No. 61/774,665, filed Mar. 8, 2013, the disclosure of which is hereby incorporated by reference in its entirety.

FIELD OF THE INVENTION

The present invention relates generally to a gas delivery and scavenging device for use in the medical field. More particularly, the present invention relates to a mask for delivering therapeutic gases to medical patients and scavenging exhaled gases from medical patients.

BACKGROUND

Therapeutic gases, including oxygen, anesthetic agents, and the like, are commonly administered to medical patients during treatment. The therapeutic gases may be administered to the patient through a mask that covers the patient's nose and mouth.

Some therapeutic gases pose well-known health risks to medical workers and patients. For example, medical workers exposed to anesthesia could lose consciousness or die as a result of the exposure. Further, even small amounts of anesthesia inhaled by medical workers could diminish their capacity to provide competent care to patients, thereby jeopardizing the safety of the patients under their care.

Patients may continue to exhale residual therapeutic gases even after delivery of the therapeutic gases has ended. In turn, the residual gases exhaled may be of sufficient quantity to pose the aforementioned risks to the safety of medical workers and other patients if not properly scavenged. Thus, there exists a need for scavenging and control of therapeutic gases exhaled by medical patients.

U.S. Pat. No. 6,357,437 ("the '437 patent") describes a pliable medical mask with an oxygen port and a recovery port extending through an upper portion of the mask. The recovery port in the '437 patent is attached to an evacuation assembly including openings that are in fluid communication with the surrounding area. The '437 patent states that the channels through the evacuation assembly allow waste gases to leak into the surrounding area. Further, the oxygen port and the recovery port in the '437 patent are free to pivot at their respective mask attachment points, given their independent arrangement and the flexible nature of the mask shell, thereby making it difficult to maintain effective relative positioning between the ports within the mask.

U.S. Pat. No. 7,114,498 ("the '498 patent") describes a medical face mask including a shell that is fabricated of a flexible material, and a fresh-gas inflow tube and an exhaust-gas outflow tube, both of which are connected to an upper nasal portion of the mask. However, clinical use of such a mask has revealed that typical central vacuum systems may not provide sufficient scavenging potential to prevent leakage of exhaled gases from the mask into the surrounding area.

Accordingly, there exists a need for an improved mask that delivers therapeutic gases to medical patients and scavenges exhaled gases away from the surrounding area.

SUMMARY OF THE INVENTION

The foregoing needs are met, to a great extent, by embodiments of the present invention that provide a respiratory mask for a medical patient for delivering therapeutic gases to the patient and scavenging exhaled gases away from the patient and the surrounding area.

In accordance with one embodiment of the present invention, a respiratory mask for a medical patient comprises a shell and a flow coupling. The shell includes an upper portion configured to cover a nose of the patient and a lower portion configured to cover a mouth of the patient, where an internal surface of the shell defines an interior volume of the mask. The flow coupling includes a body, a supply flow passage extending through the flow coupling, a scavenging flow passage extending through the flow coupling, and a septum within the body that separates the supply flow passage from the scavenging flow passage. The supply flow passage is fluidly coupled to a first aperture that extends through the upper portion of the shell, and the scavenging flow passage is fluidly coupled to a second aperture that extends through the lower portion of the shell.

In accordance with another embodiment of the present invention, a respiratory mask for a medical patient comprises a shell and a flow coupling. The shell includes a base that defines a peripheral edge, a lower portion having a top, a bottom, and a maximum depth extending from the base, and an upper portion disposed above the lower portion. The upper portion includes an overhanging surface that extends from the top of the lower portion in a direction away from the base, where the overhanging portion extends away from the base beyond the maximum depth of the lower portion. An interior volume of the mask is defined by an internal surface of the shell. The flow coupling includes a body, a supply flow passage extending through the flow coupling, a scavenging flow passage extending through the flow coupling, and a septum within the body that separates the supply flow passage from the scavenging flow passage. The supply flow passage is fluidly coupled to a first aperture that extends through the upper portion of the shell, and the scavenging flow passage is fluidly coupled to a second aperture that extends through the lower portion of the shell.

In accordance with yet another embodiment of the present invention, a flow coupling for a respiratory mask comprises a body, a supply flow passage disposed through the flow coupling, a scavenging flow passage disposed through the flow coupling, a septum within the body that separates the supply flow passage from the scavenging flow passage; and a first extension tube extending from a first end of the body and including a first lumen therein. The first lumen is in fluid communication with the supply flow passage and an aperture disposed at a distal end of the first extension tube.

A respiratory mask according to embodiments of the present invention may be used to deliver a therapeutic gas to a wearer of the mask. Further, a respiratory mask according to embodiments of the present invention may be used to scavenge gases away from a wearer of the mask. Moreover, a respiratory mask according to the present invention may be used to sample gases for analysis.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is understood, therefore, that the claims include such equivalent constructions insofar as they do not depart from the spirit and scope of the present invention.

BRIEF DESCRIPTION OF THE DRAWINGS

FIG. 3 is a cross-sectional view taken along section 3-3 of the shell in FIG. 2.

FIG. 4 is a cross-sectional view taken along section 3-3 of the respiratory mask for a medical patient in FIG. 2.

DETAILED DESCRIPTION

Figures 1, 2:
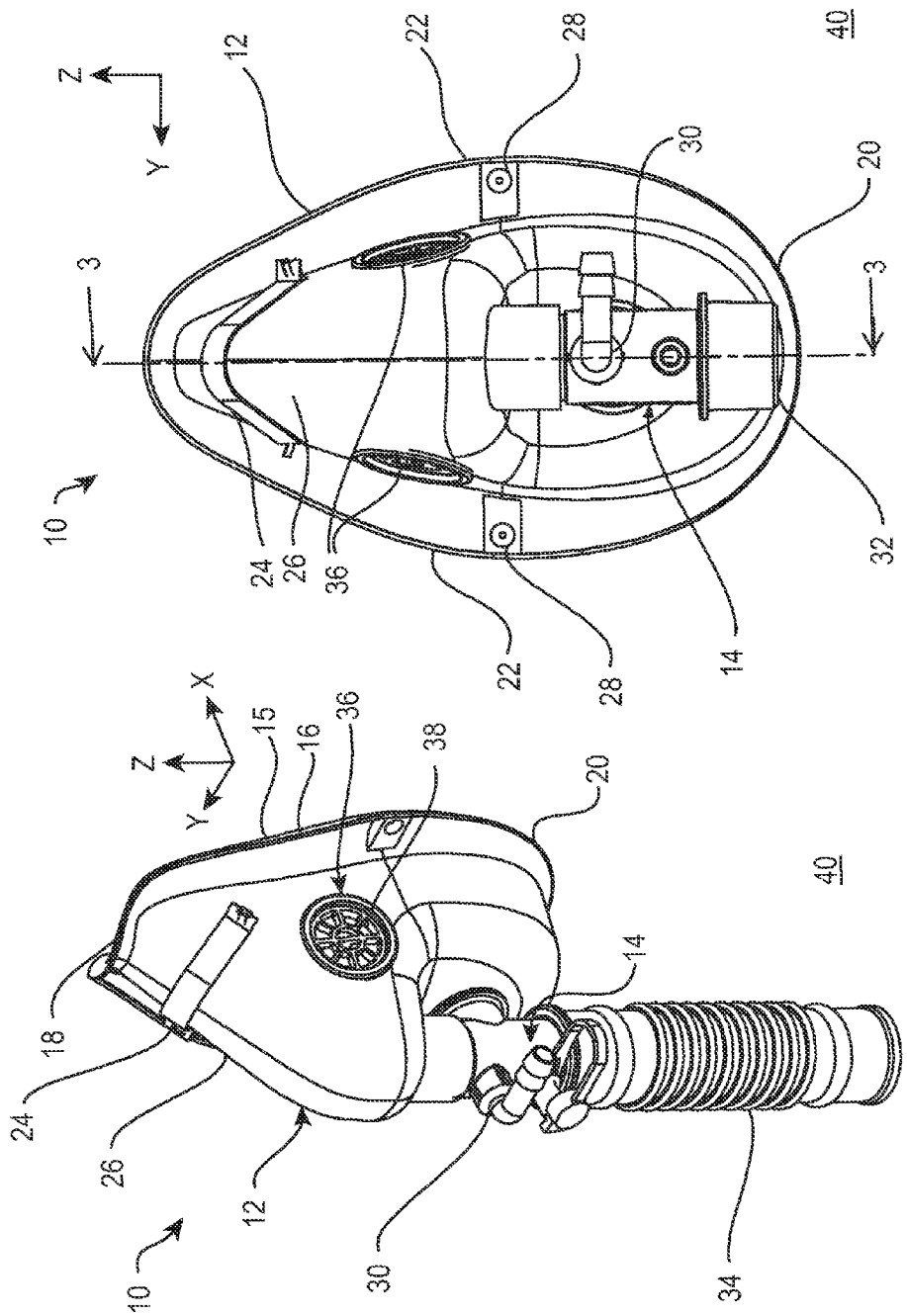
FIG. 1 is a perspective view illustrating a respiratory mask for a medical patient according to an embodiment of the invention.
FIG. 2 is a front view illustrating a respiratory mask for a medical patient according to another embodiment of the invention.

Embodiments of the invention will now be described with reference to the drawing figures, in which like reference numerals refer to like parts throughout.

Referring now to FIGS. 1 and 2, it will be appreciated that FIG. 1 is a perspective view illustrating a respiratory mask 10 for a medical patient according to an embodiment of the invention, and FIG. 2 is a front view illustrating a respiratory mask 10 for a medical patient according to another embodiment of the invention.

The respiratory mask 10 includes a shell 12 and a flow coupling 14. The mask 10 has a base 15 that is configured to engage the face of a medical patient, and that defines a peripheral edge 16. The base 15 may include a nose engaging portion 18 that is configured to engage the bridge of the patient's nose. Further the base 15 may include a chin engaging portion 20 and cheek engaging portions 22 that are configured to engage the contours of a patient's chin and cheeks, respectively. A deformable strip 24 may attach to an outer surface 26 of the shell 12, where the deformable strip may aid in shaping the shell 12 around the contour of the patient's nose. The shell 12 may also include attachment points 28 for attaching a retaining strap (not shown), such as an elastic strap, for example, to the shell 12.

The flow coupling 14 has a supply flow inlet port 30, whereby a supply of therapeutic gases enters the flow coupling 14. The therapeutic gases delivered to the respiratory mask 10 through the flow coupling 14 may include air, oxygen, anesthetic agents, combinations thereof, or other therapeutic gases known to persons of ordinary skill in the art. Further, the flow coupling 14 has a scavenging flow outlet port 32, whereby scavenged gases exit the flow coupling. A corrugated extension tube 34 may be attached to the scavenging flow outlet port 32, where the corrugated structure of the tube provides compliance in bending with simultaneous compressive hoop strength to resist sub-atmospheric pressures within the corrugated extension tube 34.

The shell 12 may include one or more check valves 36 disposed in valve apertures 38 through the shell 12. The check valves 36 allow gas to flow from the local environment 40 into the interior of the shell 12 via the valve apertures 38 when the pressure within the interior of the shell 12 is sufficiently lower than a pressure of the local environment 40. Else, the check valves restrict or seal gases from flowing from the interior of the shell 12 to the local environment 40 via the valve apertures 38 when the pressure within the interior of the shell is not sufficiently lower than a pressure of the local environment 40. The check valves 36 allow a patient to draw in air from the local environment 40 in the event that gas supply to the supply flow inlet port 30 is insufficient.

FIG. 3 is a cross-sectional view taken along section 3-3 of the shell 12 in FIG. 2. The shell 12 includes an upper portion 42 that is configured to cover a nose of the patient and a lower portion 44 that is configured to cover a mouth of the patient. The upper portion 42 may have a nose-like profile in the xz-plane, as illustrated in FIG. 3. The lower portion 44 has a top 44a and a bottom 44b, and extends a maximum depth 45 from the base 15 of the shell 12 in the x-direction.

An interior surface 46 of the shell 12 defines an interior volume 48 of the mask, where the interior surface 46 of the shell 12 is opposite the outer surface 26 of the shell 12. The interior surface 46 of the shell 12 spans both the upper portion 42 of the shell 12 and the lower portion 44 of the shell 12, such that both the upper portion 42 and the lower portion 44 contribute to defining the interior volume 48.

The upper portion 42 of the shell 12 defines an inlet aperture 50 therethrough, whereby therapeutic gases may enter the interior volume 48 of the shell 12 according to flow arrow 54. Further, the lower portion 44 of the shell 12 defines an exit aperture 52 therethrough, whereby gases exhaled by the patient may exit the interior volume 48 of the shell 12 according to flow arrow 56.

In one embodiment of the present invention, the upper portion 42 of the shell 12 includes an overhanging portion 58. The overhanging portion 58 projects away from the peripheral edge 16 of the shell 12 in the x-direction above the lower portion 44, such that the lower portion 44 is disposed below the overhanging portion 58 in the z-direction. Further, the lower portion 44 may project away from the overhanging portion 58 in the z-direction. In another embodiment of the present invention, a portion of the shell 12 between the overhanging portion 58 and the lower portion 44 demarcates the boundary between the upper portion 42 and the lower portion 44 of the shell 12. Throughout the present disclosure, each of the x-direction, y-direction, and z-direction are orthogonal to one another.

In one embodiment of the present invention, the inlet aperture 50 through the shell 12 is defined by the overhanging portion 58. In such an embodiment, a line 60 normal to a plane lying in the exit aperture 52 may intersect a line 62 normal to a plane lying in the inlet aperture 50.

The exit aperture 52 may be disposed through the shell 12 at a location that advantageously locates an axis 60 of the exit aperture 52 below the mouth of a wearer of the mask 10.

Alternatively, the exit aperture 52 may be disposed through the shell 12 at a location that advantageously locates the entire exit aperture 52 below the mouth of a wearer of the mask 10.

In an embodiment of the present invention, a vertical distance 47 along that z-direction between the top 44a and the bottom 44b of the lower portion 44 advantageously ranges from about 1.7 inches to about 2.7 inches. In another embodiment with a different configuration, the vertical distance 47 advantageously ranges from about 1.95 inches to about 2.45 inches. In yet another advantageous embodiment, the vertical distance 47 is about 2.2 inches.

In an embodiment of the present invention, a vertical distance 49 along the z-direction from the bottom 44b of the lower portion 44 to the line 60 through the exit aperture 52 of the shell 12 advantageously ranges from about 1.35 inches to about 1.85 inches. In another embodiment with a different configuration, the vertical distance 49 advantageously ranges from about 1.1 inches to about 2.1 inches. In yet another advantageous embodiment, the vertical distance 49 is about 1.6 inches.

FIG. 4 is a cross-sectional view taken along section 3-3 of the respiratory mask 10 for a medical patient in FIG. 2. The respiratory mask 10 includes a shell 12 and a flow coupling 14. The flow coupling may include a body 64 with an elongated monolithic shape, which may include a generalized cylindrical shape. The body 64 may have a circular cross section, a polygonal cross section, an oval cross section, or the like.

The body 64 has a first shell engagement portion 66 that engages the shell 12, such that the supply flow inlet port 30 is fluidly coupled to the interior volume 48 of the shell 12 through a supply flow outlet port 68. The first shell engagement portion 66 may be an external surface of the body 64. In an advantageous embodiment of the present invention, the supply flow outlet port 68 is disposed in a portion of the interior volume 48 of the shell 12 that is defined by the upper portion 42 of the shell 12. In yet another advantageous embodiment of the present invention the shell 12 seals around the first shell engagement portion 66 of the flow coupling 14.

Figure 5:
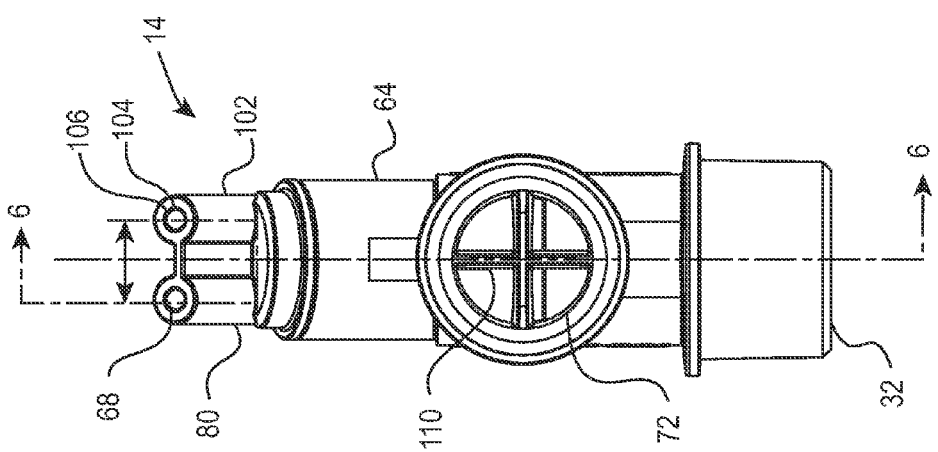
FIG. 5 is a rear view of a flow coupling for a respiratory mask according to another embodiment of the invention.

The body 64 has a second shell engagement portion 70 that engages the shell 12, such that the scavenging flow outlet port 32 of the body 64 is fluidly coupled to the interior volume 48 of the shell 12 through a scavenging flow inlet port 72, best shown in FIG. 5. In an advantageous embodiment of the present invention, scavenging flow inlet port 72 (see FIG. 5) is disposed in a portion of the interior volume 48 of the shell 12 that is defined by the lower portion 44 of the shell 12. In another advantageous embodiment of the present invention, the shell 12 seals around the second shell engagement portion 70 of the flow coupling 14.

Figure 6:
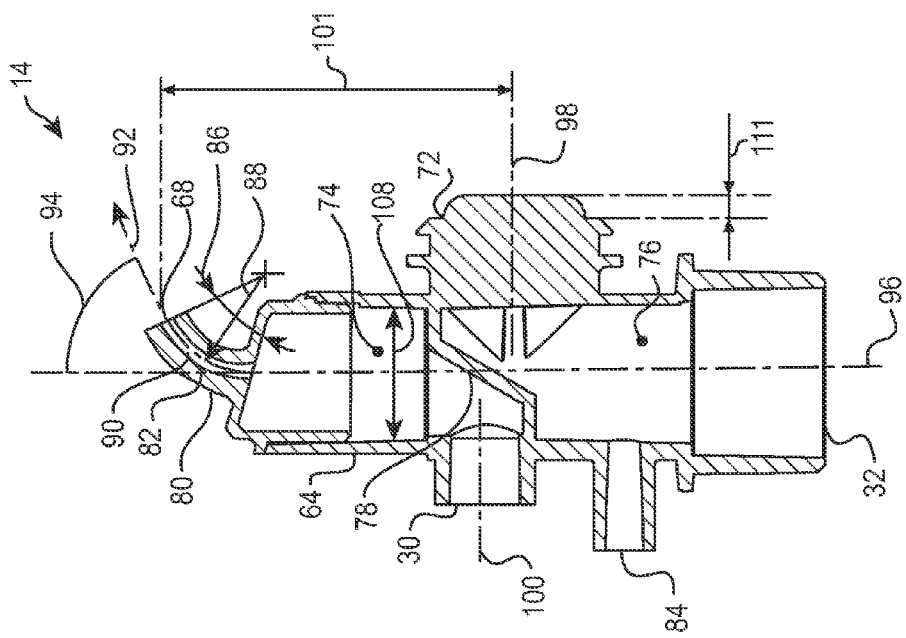
FIG. 6 is a cross-sectional view taken along section 6-6 of the respiratory mask for a medical patient in FIG. 5.

Referring now to FIGS. 5 and 6, it will be appreciated that FIG. 5 is a rear view illustrating a flow coupling for a respiratory mask 10 according to an embodiment of the invention, and that FIG. 6 is a cross-sectional view taken along section 6-6 of the respiratory mask 10 for a medical patient in FIG. 5.

The body 64 defines a supply flow passage 74 therein. The supply flow passage 74 of the body 64 is in fluid communication with both the supply flow inlet port 30 and the supply flow outlet port 68. Further, the body 64 defines a scavenging flow passage 76 therein. The scavenging flow passage 76 is in fluid communication with both the scavenging flow inlet port 72 and the scavenging flow outlet port 32. The flow coupling 14 may include a gas sampling port 84, through which scavenged gases may be sampled for analysis, that is in fluid communication with the scavenging flow passage 76. In one embodiment the sampled gases are analyzed to determine the patient's end tidal $CO_2$ concentration.

In an advantageous embodiment of the present invention, the supply flow passage 74 is separated from the scavenging flow passage 76 by a septum 78 disposed within the body 64. The septum 78 may be configured to isolate the supply flow passage 74 from the scavenging flow passage 76, such that the supply flow passage 74 is not in fluid communication with the scavenging flow passage 76 within the body 64 of the flow coupling 14.

The flow coupling 14 may include one or more extension tubes 80 that projects from an end of the body 64. The extension tube 80 defines a lumen 82 therein such that the lumen 82 is in fluid communication with both the supply flow passage 74 and the supply flow outlet port 68. The extension tube 80 may include a straight cylindrical tube, a plurality of straight cylindrical tubes joined via miter joints, a curved shape, a toroidal shape, or the like. It will be appreciated that the term cylindrical, as used herein, includes generalized cylindrical shapes, which may have any cross section, not limited to a circular cross section.

Alternatively, the flow coupling 14 may not include any extension tubes projecting from the end of the body 64. In such a configuration without an extension tube, the supply flow outlet port 68 may be defined by an aperture through the end of the flow coupling 14.

Applicants have discovered advantageous relationships between the velocity of therapeutic gases exiting the supply flow outlet port 68 and scavenging performance of the respiratory mask 10 by promoting beneficial interaction between a jet of therapeutic gases exiting the supply flow outlet port 68 and the patient's nose. In one embodiment of the present invention, an internal flow area of the lumen 82 between about 0.06 square inches and about 0.07 square inches effects an advantageous velocity of therapeutic gases exiting the supply flow outlet port 68. In another embodiment of the present invention, an internal diameter of the lumen 82 between about 0.28 inches and about 0.30 inches effects an advantageous velocity of therapeutic gases exiting the supply flow outlet port 68.

In the non-limiting embodiment illustrated in FIG. 6, the extension tube 80 defines a sector of a toroidal surface. In one advantageous embodiment, the sector of the toroidal surface extends over a sector angle 86 ranging from about 39 degrees to about 59 degrees. In another advantageous embodiment, corresponding to a different configuration of the respiratory mask 10, the sector of the toroidal surface extends over a sector angle 86 ranging from about 44 degrees to about 54 degrees. In yet another advantageous embodiment, the sector of the toroidal surface may have a radius of curvature 88, with respect to a centerline 90 of the lumen 82, that ranges from about 0.3 inches to about 0.4 inches.

As best shown in FIG. 6, a direction of flow 92 leaving the supply flow outlet port 68 forms an angle 94 with a longitudinal axis 96 of the body 64. Applicants have discovered advantageous relationships between the supply flow outlet angle 94 and scavenging performance of the respiratory mask 10 by promoting beneficial interaction between a jet of therapeutic gases exiting the supply flow outlet port 68 and the patient's nose. In one embodiment, the angle 94 is between about 45 degrees and about 75 degrees to advantageously align the direction of flow 92 leaving the supply flow outlet port 68 with a direction of flow entering the patients nose. In another embodiment corresponding to a different configuration of the mask 10, the angle 94 is between about 55 degrees and about 70 degrees to advantageously align the direction of flow 92 leaving the supply flow outlet port 68 with a direction of flow entering the patients nose.

In an advantageous embodiment of the present invention, an axis 98 of the scavenging flow inlet port 72 is substantially perpendicular to the longitudinal axis 96 of the body 64. In another advantageous embodiment of the present invention, an axis 100 of the supply flow inlet port 30 is substantially perpendicular to the longitudinal axis 96 of the body 64.

In an embodiment of the present invention, a vertical distance 101 from the axis 98 of the scavenging flow inlet port 72 to the supply flow outlet port 68 advantageously ranges from about 0.55 inches to about 2.55 inches. In another embodiment with another configuration, the vertical distance 101 advantageously ranges from about 1.05 inches to about 2.05 inches. In yet another advantageous embodiment of the present invention, the vertical distance 101 is about 1.6 inches.

As best shown in FIG. 5, the flow coupling 14 may include two extension tubes, 80 and 102, where the extension tube 102 also projects from an end of the body 64, similar to extension tube 80. The extension tube 102 defines a lumen 104 therein such that the lumen 104 is in fluid communication with both the supply flow passage 74 and a supply flow outlet port 106. The extension tube 102 may include a straight cylindrical tube, a plurality of straight cylindrical tubes joined via miter joints, a curved shape, a toroidal shape, or the like. The dimensions and flow path of the lumen 104 may be the same as or different from the dimensions and flow path of the lumen 82.

The supply flow passage may include a lumen 108 located upstream of the extension tube 80 in a direction of supply flow, such that a cross sectional area of the lumen 82 transverse to a bulk flow direction through the lumen 82 is smaller than a cross sectional area of the lumen 108 transverse to a bulk flow direction through the lumen 108.

As best shown in FIG. 5, the flow coupling 14 may include at least one flow channel partition 110 disposed within the scavenging flow passage 76 (see FIG. 6). The at least one flow channel partition 110 may have a plate structure extending across the scavenging flow passage 76. In an advantageous embodiment of the present invention, the at least one flow channel partition 110 may include two flow channel partitions oriented perpendicular to one another.

The scavenging flow inlet port 72 may have an internal flow area, normal to a direction of bulk flow, that advantageously ranges from about 0.1 square inches to about 0.8 square inches. Alternatively, the scavenging flow inlet port 72 may have an internal diameter that ranges from about 0.3 (10 mm) inches to about 1.0 inches (25 mm).

Figure 8:
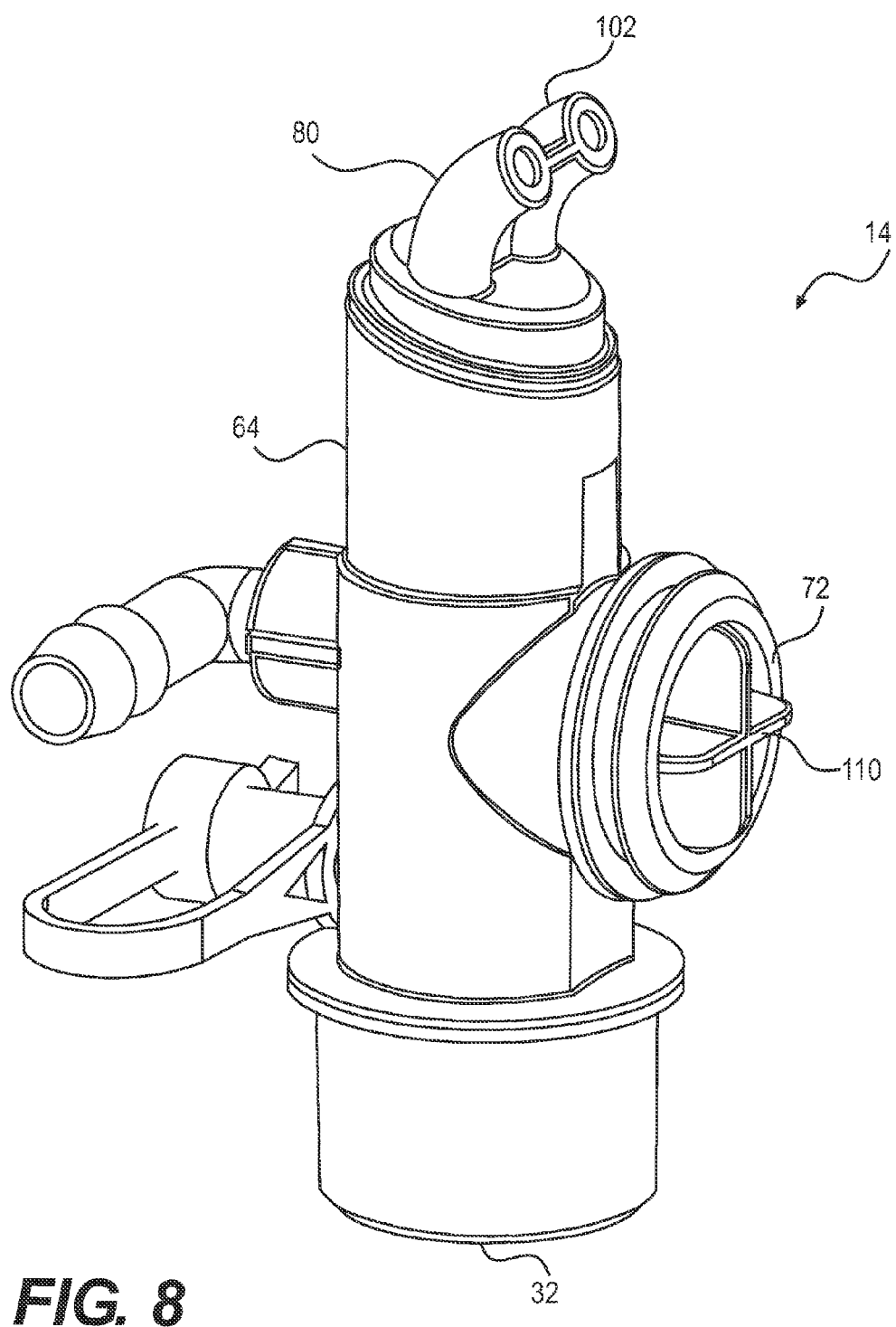
FIG. 8 is a perspective view illustrating a respiratory mask for a medical patient according to yet another embodiment of the invention.

As best shown in FIG. 8, the at least one flow channel partition 110 may extend beyond the scavenging flow inlet port 72, thereby avoiding suction lock between the scavenging flow inlet port 72 and a face of the wearer of the mask 10. Suction lock between the scavenging flow inlet port 72 and the face of the wearer of the mask 10 is disadvantageous because it could block or unduly limit scavenging flow out of the mask 10 and into the suction source.

Referring to FIG. 6, the at least one flow channel partition 110 may advantageously extend beyond the scavenging flow inlet port 72 by a horizontal distance 111 in the x-direction that ranges from about 0.03 inches to about 0.43 inches. In another embodiment of the present invention with a different configuration, the horizontal distance 111 advantageously ranges from about 0.13 inches to about 0.33 inches. In yet another advantageous embodiment of the present invention, the horizontal distance 111 is about 0.23 inches.

The flow coupling 14 may be fabricated from a substantially rigid material such as, a plastic including, for example, acrylic, polyethylene, polymide, polyamide, or polyvinyl chloride; metals including, for example, aluminum; combinations thereof, or other similar materials known to persons of ordinary skill in the art.

Figure 7:
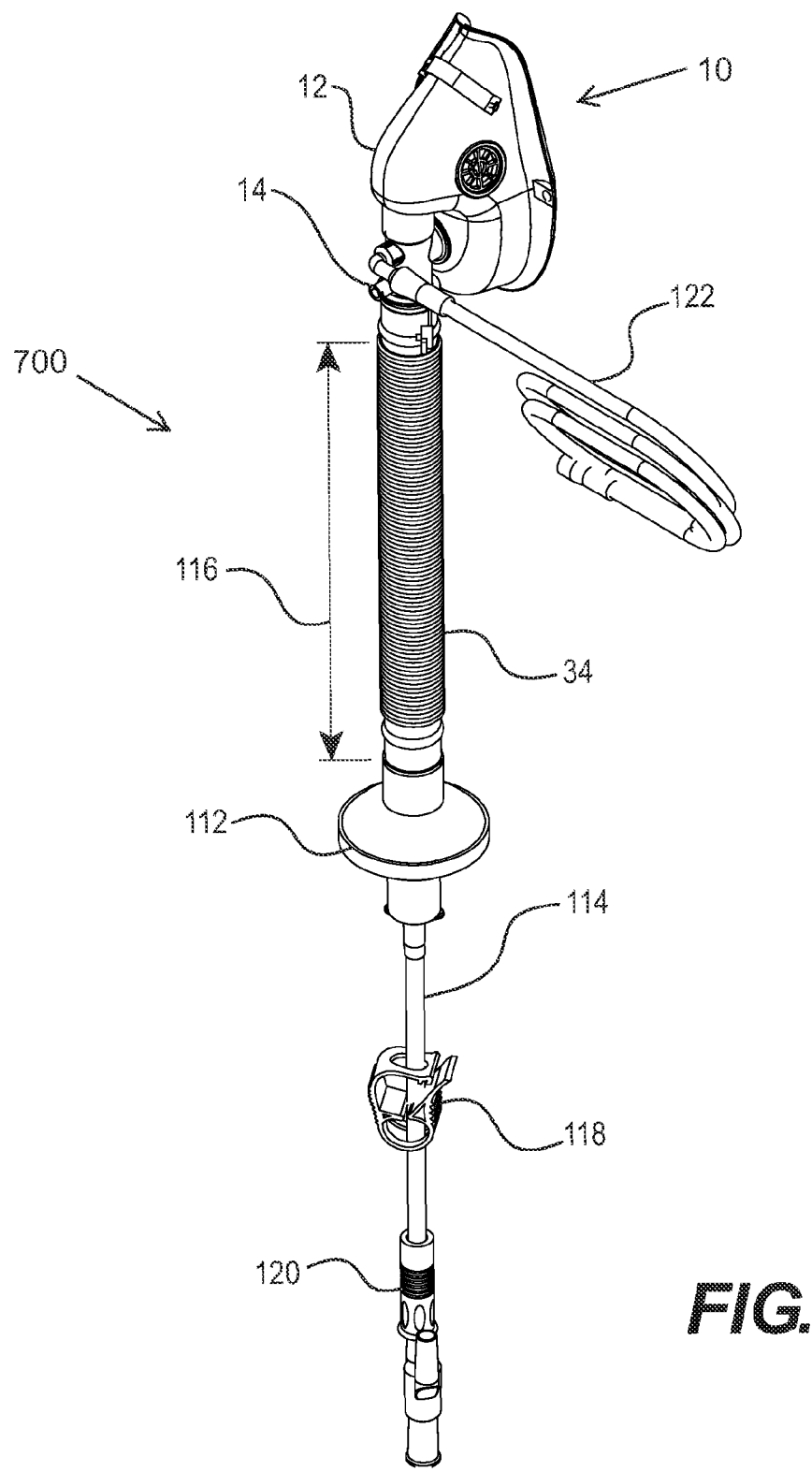
FIG. 7 is a perspective view illustrating a system for a respiratory mask for a medical patient according to another embodiment of the invention.

FIG. 7 is a perspective view illustrating system 700 for a respiratory mask 10 for a medical patient according to another embodiment of the invention. The respiratory mask system 700 includes a filter 112 that is fluidly coupled to the corrugated extension tube 34 and a suction tube extension 114. In one embodiment, the corrugated extension tube 34 has an axial length 116 not less than about 24 inches to provide sufficient compliance to enable the corrugated extension tube 34 to be routed from the flow coupling 14 across the patient's body and to the filter 112, without disrupting the position of the mask on the patient's face.

Further, Applicants have discovered advantageous relationships between the corrugated extension tube 34 axial length 116 and scavenging performance of the respiratory mask 10, at least in part because a volume within the corrugated extension tube 34 provides a beneficial vacuum reservoir function. Accordingly, in other embodiments having a different configuration of the respiratory mask 10, the corrugated extension tube 34 has an axial length 116 not less than about 60 inches to promote the vacuum reservoir effect of the corrugated extension tube.

In one embodiment of the present invention, the corrugated extension tube 34 has an internal flow area, normal to a direction of bulk flow, that advantageously ranges from about 0.12 square inches to about 1.5 square inches. In another embodiment of the present invention with a different configuration, the corrugated extension tube 34 has an internal flow area that advantageously ranges from about 0.4 square inches to about 0.7 square inches.

In one embodiment of the present invention, the corrugated extension tube 34 has an internal diameter that advantageously ranges from about 0.4 inches (10 mm) to about 1.4 inches (35 mm). In another embodiment of the present invention with a different configuration, the corrugated extension tube 34 has an internal diameter that advantageously ranges from about 0.7 inches (18 mm) to about 0.9 inches (24 mm).

The suction tube extension 114 may be coupled to a suction source (not shown) through a connector 120. A clamp 118 may be disposed on the suction tube extension 114 to selectively throttle the suction pressure from the suction source or isolate the shell 12 from the suction source.

According to an advantageous embodiment of the present invention, the respiratory mask 10 is applied to the face of a medical patient and secured to the patient using an elastic strap or the like. The shell 12 of the respiratory mask 10 is positioned on the patient's face such that the nose engaging portion 18 rests on a bridge of the patient's nose, the chin engaging portion 20 rests on the patient's chin, and the cheek engaging portions 22 rest on the patient's cheeks. The scavenging flow passage 76 is fluidly coupled to a suction source via the corrugated extension tube 34 and optionally through the filter 112 and the suction tube extension 114. Further, the supply flow passage 74 of the flow coupling 14 may be fluidly coupled to a supply flow source (not shown) by attaching a supply flow tube 122 (see FIG. 7) to the supply flow inlet port 30.

The patient inhales therapeutic gases delivered to a portion of the shell 12 interior volume 48 defined by the upper portion 42 of the shell 12, and exhales into a portion of the shell 12 interior volume 48 defined by the lower portion 44 of the shell 12. The location of the supply flow outlet port 68 in close proximity to the patient's nose within the upper portion 42 of the shell 12, and the location of the scavenging flow inlet port 72 below the patient's nose and within the lower portion of the shell 12, combine to effect a unidirectional bulk flow path 126 (see FIG. 4) within the shell 12.

Applicants have discovered that the unidirectional bulk flow path 126 established within the respiratory mask 10 reduces the dilution of incoming therapeutic gases with exhaled gases within the interior volume 48 of the shell 12, thereby decreasing the driving potential for leakage of exhaled gases across the interface of the peripheral edge 16 of the shell 12 and the patient's face. Indeed, dilution of the incoming therapeutic gases with gases exhaled by the patient increases the flow rate of the therapeutic gases required to achieve the desired therapeutic effect. In turn, increasing the flow rate of therapeutic gases supplied to the interior volume 48 of the shell 12 increases the driving potential for leakage past the interface between the peripheral edge 16 of the shell 12 and the patient's face by increasing the pressure within the shell 12.

Moreover, dilution of the incoming therapeutic gases with exhaled gases increases the amount of therapeutic gases that bypass the patient's respiratory system by flowing directly from the supply flow outlet port 68 to the scavenging flow inlet port 72. In turn, bypass of the therapeutic gases around the patient's respiratory system increases the required scavenging flow by the suction source, not to mention wasting the bypassed therapeutic gas. Accordingly, embodiments of the present invention address the above-noted deficiencies in conventional approaches by decreasing dilution of therapeutic gases within the interior volume 48 of the shell 12 by effecting a unidirectional bulk flow path 126 within the interior volume 48 of the shell 12.

Further advantageous aspects of the present invention offer improvements over conventional approaches by fixing the locations and orientations of the supply flow outlet port 68 and the scavenging flow inlet port 72 relative to one another by providing a substantially rigid flow coupling 14. Thus, unlike the conventional approaches, embodiments of the present invention do not rely on the stiffness of the shell 12 to fix the location or orientation of the supply flow outlet port 68 relative to the scavenging flow inlet port 72, thereby promoting careful tailoring of the bulk flow path within the respiratory mask 10.

The respiratory mask 10 may be used to scavenge gases exhaled by a wearer of the respiratory mask 10, scavenge unused therapeutic gases that bypass the respiratory system of a wearer after delivery to the respiratory mask 10, or combinations thereof. In some embodiments the wearer of the respiratory mask 10 is a medical patient. In other embodiments the wearer of the respiratory mask 10 is a medical patient undergoing a surgical procedure.

In one embodiment, the gases scavenged from the respiratory mask 10 include air enriched with additional oxygen. In another embodiment, the gases scavenged from the respiratory mask 10 include oxygen and anesthetic agents.

The respiratory mask 10 may be used to deliver a therapeutic gas to a medical patient without scavenging. Further, the respiratory mask 10 may be used to scavenge gases without delivering a therapeutic gas. In one embodiment, the respiratory mask 10 is used to sample a gas exhaled from a medical patient for end tidal $CO_2$ analysis. In another embodiment, the respiratory mask 10 is used to deliver air to a medical patient and sample a gas exhaled from a medical patient for end tidal $CO_2$ analysis. In yet another embodiment, the respiratory mask 10 is used to deliver air, oxygen, or combinations thereof to a wearer of the respiratory mask 10.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A respiratory mask for a medical patient, comprising:
a shell including an upper portion configured to cover a nose of the patient and a lower portion configured to cover a mouth of the patient, an internal surface of the shell defining an interior volume of the respiratory mask; and
a flow coupling having a body separate from and outside the shell, the body being engaged with the shell and defining a longitudinal axis of the body,
a supply flow passage extending through the flow coupling at least partially along the longitudinal axis of the body,
a scavenging flow passage extending through the body of the flow coupling, and
a septum within the body of the flow coupling that separates the supply flow passage from the scavenging flow passage, the supply flow passage and scavenging flow passage both being contained within the body of the flow coupling,
the supply flow passage being fluidly coupled to a first aperture that extends through the upper portion of the shell, and
the scavenging flow passage being fluidly coupled to a second aperture that extends through the lower portion of the shell, and
wherein a scavenging flow through the second aperture is in a direction that is perpendicular to the longitudinal axis of the body, and
wherein the flow coupling partially fits into the first aperture and the second aperture.

2. The respiratory mask of claim 1, wherein an outlet port of the supply flow passage is disposed within a portion of the interior volume defined by the upper portion of the shell.

3. The respiratory mask of claim 1, wherein an outlet port of the supply flow passage and an inlet port of the scavenging flow passage are configured and arranged in the respiratory mask to effect a uni-directional bulk flow of gas through the interior volume of the respiratory mask.

4. The respiratory mask of claim 1, further comprising:
a first extension tube that extends from a first end of the body into a volume defined by the upper portion of the shell,
wherein the first extension tube includes
a first lumen defined therein, and
a first outlet port disposed at a distal end of the first extension tube, and
wherein the first outlet port is in fluid communication with the supply flow passage via the first lumen.

5. The respiratory mask of claim 4, wherein
a direction of a flow leaving the first outlet port of the first extension tube forms an angle with a longitudinal axis of the body that is between about 45 degrees and about 75 degrees.

6. The respiratory mask of claim 4, wherein the first extension tube is curved.

7. The respiratory mask of claim 4, wherein the first extension tube defines a sector of a toroidal surface.

8. The respiratory mask of claim 4, further comprising:
a second extension tube that extends from the first end of the body into the volume defined by the upper portion of the shell,
wherein the second extension tube includes
a second lumen defined therein, and
a second outlet port disposed at a distal end of the second extension tube, and
wherein the second outlet port is in fluid communication with the supply flow passage via the second lumen.

9. The respiratory mask of claim 4, wherein
the body of the flow coupling defines a third lumen, the third lumen forming a portion of the supply flow passage, and
a cross-sectional area of the first lumen is smaller than a cross sectional area of the third lumen.

10. The respiratory mask of claim 1, wherein the body has a substantially cylindrical shape.

11. The respiratory mask of claim 1, wherein the flow coupling is constructed of a substantially rigid material.

12. The respiratory mask of claim 4, wherein the first extension tube defines a sector of a toroidal surface.

13. The flow coupling of claim 12, wherein the toroidal surface extends over a sector angle ranging from about 39 degrees to about 59 degrees.

14. The flow coupling of claim 12, wherein the first lumen has a cross sectional flow area ranging from about 0.06 square inches to about 0.07 square inches.

15. The respiratory mask of claim 4, wherein
the body includes a second lumen therein, and
a cross sectional area of the first lumen is smaller than a cross sectional area of the second lumen.

16. The respiratory mask of claim 4, wherein a vertical distance from an aperture disposed at a distal end of the first extension tube to an axis of the scavenging flow passage ranges from about 0.6 inches to about 2.6 inches.

17. The respiratory mask of claim 1, wherein a vertical height of the lower portion ranges from about 1.1 inches to about 2.1 inches.

18. The respiratory mask of claim 1, wherein a vertical height from a bottom of the lower portion to an axis of the second aperture through the shell ranges from about 1.35 inches to about 1.85 inches.

19. The respiratory mask of claim 1, wherein the second aperture is disposed through the shell such that an axis of the second aperture is located below the mouth of the patient.

20. The respiratory mask of claim 1, wherein the second aperture is disposed through the shell such that the second aperture is entirely located below the mouth of the patient.

* * * * *